United States Patent [19]

Rhoads et al.

[11] 4,228,405
[45] Oct. 14, 1980

[54] LOAD ACTIVATED NORMALLY QUIESCENT WAVEFORM GENERATOR

[75] Inventors: Kevin G. Rhoads, Lehighton, Pa.; George M. Plotkin, Massapequa Park, N.Y.

[73] Assignee: VRL Growth Associates, Incorporated, Boston, Mass.

[21] Appl. No.: 32,603

[22] Filed: Apr. 23, 1979

Related U.S. Application Data

[63] Continuation of Ser. No. 737,641, Nov. 1, 1976, abandoned, which is a continuation-in-part of Ser. No. 722,313, Sep. 10, 1976, Pat. No. 4,120,305.

[51] Int. Cl.² ........................................... H03K 3/30
[52] U.S. Cl. ...................................... 331/65; 331/112
[58] Field of Search ........................ 331/65, 112, 146; 128/419 S; 231/2 E; 273/84 ES; 361/232

[56] References Cited

U.S. PATENT DOCUMENTS

| 2,663,806 | 12/1953 | Darlington | 307/315 |
| 2,881,380 | 4/1959 | Krüger | 331/112 X |
| 2,984,766 | 5/1961 | Moore | 331/112 X |
| 3,059,141 | 10/1962 | Fischman | 331/112 X |
| 3,608,524 | 9/1971 | Waltz | 231/2 E X |

*Primary Examiner*—Siegfried H. Grimm
*Attorney, Agent, or Firm*—Jim Zegeer

[57] ABSTRACT

There is disclosed a novel compact power oscillator which is normally quiescent until applied to a load, to produce, under load, a unique waveform which has a unique application to self-protective devices and medical uses. The oscillator includes a high gain inverting amplifier, preferably a Darlington pair constituted by a germanium output transistor driven by a small signal transistor, a transformer, a D.C. source such as a battery, and a pair of output electrodes.

5 Claims, 5 Drawing Figures

FIG 3(A) LOADED

FIG 3(B) UNLOADED

T = PERIODE OF FUNDAMENTAL
$V_{pL}$ = PEAK VOLTAGE
$V_{AVE}$ = AVERAGE VOLTAGE

*NORMALLY FOUR BUT OCCASIONALY FIVE OR SIX LOCAL MAXIMA WERE OBSERVED IN THIS AREA OVER A WIDE RANGE OF CONDITIONS WITH VARIOUS PROTOTYPE CIRCUIT ELEMENTS.

LOAD ACTIVATED NORMALLY QUIESCENT WAVEFORM GENERATOR

This application is a continuation of application Ser. No. 737,641 filed Nov. 1, 1976 and now abandoned, which is a continuation-in-part of application Ser. No. 722,313 filed Sept. 10, 1976 and now U.S. Pat. No. 4,120,305.

BACKGROUND OF THE INVENTION

The oscillator of the present invention has been developed in connection with a self-protective device for administering an electrical shock to a would-be assailant. Such shock devices are well known in the art as is exemplified by Creedon U.S. Pat. No. 1,046,985 in an early form, and in Cover U.S. Pat. No. 3,083,463 in a more recent form, the latter patent dealing in some detail with the nature of electrical currents on the human body. Still more recently, Tingley et al U.S. Pat. No. 3,917,268 discloses a particular form of relaxation oscillator in which a spark gap is used to isolate the load from the oscillator circuit per se. These patents, as well as many, many others, disclose various forms of oscillator circuits, particularly adaptable to use in applying various forms of electrical energy to the human body or animals, either for self-protection purposes or for medical treatment purposes. Some of these prior art oscillator circuits, such as Browner U.S. Pat. No. 3,025,858 utilize as a part of the oscillatory circuit the portion of the human body between the electrodes. The medical cardiac pacemaker disclosed in Greatbach U.S. Pat. No. 3,057,356 and the muscle stimulator of Moss et al's U.S. Pat. No. 3,180,338 use blocking oscillators to produce other medical use electrical pulses; and Janssen et al U.S. Pat. No. 2,965,806 and Bernstein U.S. Pat. No. 2,957,145 are further examples of blocking oscillator circuits known in the art. However, such devices are relatively complex, and require critical component selection and/or ajustment, are more expensive, and do not provide waveforms of the type disclosed herein.

THE PRESENT INVENTION

In accordance with the present invention, a normally quiescent oscillatory circuit is provided which includes a high gain inverting amplifier which, in a highly preferred embodiment, is a Darlington connected transistor pair with a germanium type PNP output transistor, an inverting transformer element for providing, by transformer action, a stepped up voltage, a power supply which, in the preferred embodiment, is a small direct current battery, and a pair of output electrodes, one of which is connected to the input base electrode of the Darlington pair and the other of which is connected to the secondary winding portion of the transformer. Normally, in the absence of a load resistance, such as a portion of the body, across the output electrodes, the circuit is normally quiescent with the only power consumed being the leakage current between the collector-emitter electrodes of the output power transistor, the input base electrode being, effectively, open circuited.

Immediately upon the presence of a load (e.g., the body portion) across the output electrodes, a small signal current is developed and applied to the base electrode of the input transistor of the Darlington pair, which by virtue of the high current gain of the Darlington pair, is amplified and applied as a current pulse to the transformer primary via the collector-emitter circuit of the output power transistor of the Darlington pair. This current pulse induces a high voltage in the secondary winding of the transformer which, through feedback action, is applied through the body portion in contact with the electrode pair as an input to the base electrode of the input transistor of the Darlington pair which is amplified so that the process continues to repeat itself until the saturation occurs.

This action induces a rather large voltage pulse which is followed by a lower sequence of oscillatory pulses. Thus, the circuit generates, under load, a waveform which, in connection with a self-protection device or system described above, breaks down the skin resistance and then couples directly into the sensory nerves, via this transient relatively lower resistance path, a signal within the passband of the nerves. Advantages of the invention are that lower power is used, the circuit remains in a quiescent state, consuming extremely small amounts of power. An important feature of the invention is that adjustment of the circuit is not critical at all and as the loading is increased or a lower resistance is applied or appears at the terminals of the electrode, the power increases. Thus, the circuit also adapts itself to the load.

The above and other objects, advantages and features of the invention will become more apparent from the following specification taken in conjunction with the accompanying drawings wherein:

DESCRIPTION OF THE DRAWINGS

FIGS. 3(a), 3(b) and 3(c) are illustrations of the preferred form of the waveform which includes one or more large voltage pulses followed by a relatively lower amplitude voltage signal.

Referring now to FIG. 1, the block diagram illustrates a power supply 10 connected via a pair of leads 11 and 12 and a switch 13 to voltage conditioning circuit 14 which has a pair of output electrodes 15 and 16 connected to the output terminals thereof. The switch 13 is diagrammatically illustrated as having an operating element 17 associated with the electrodes 15 and 16 so that power is not supplied to the oscillator circuit until desired. Of course, switch 13 may be deleted if desired.

Figure 1:
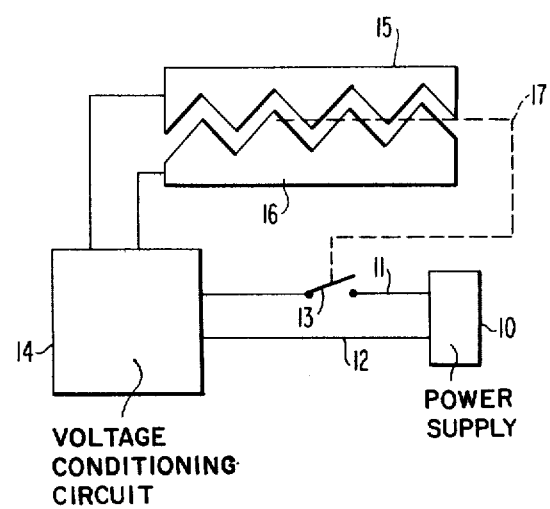
FIG. 1 is a block diagram of a circuit incorporating the invention.
Figure 2:
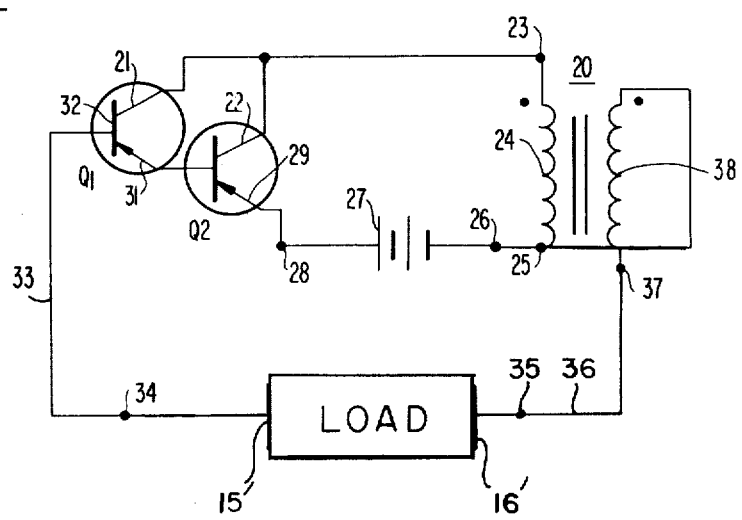
FIG. 2 is a detail schematic diagram of the invention in its most preferred form.

In its most highly preferred form, the oscillator 14, shown in detail in FIG. 2, is constituted by an inverting amplifier which is, preferably, a Darlington-connected PNP transistor pair Q1 and Q2. Collector 21 of transistor Q1 and collector 22 of transistor Q2 are commonly connected together and to terminal 23 of primary winding 24 on inverting transformer 20. Terminal 25 of primary winding 24 is connected to negative terminal 26 of a direct current power supply 27 which, in turn, has its positive terminal or pole 28 connected to emitter 29 of transistor Q2. Base 30 of transistor Q2 is directly connected to emitter 31 of transistor Q1. Base 32 of transistor Q1 is connected by a lead 33 to an output load terminal 34 whereas a second output load terminal 35 is connected by a lead 36 to terminal 37 of secondary winding 38 of transformer 20. It will be noted that the primary winding 24 and secondary winding 38 of transformer 20 have the polarity relationships indicated by the dots at the upper end of each winding which must be observed for a proper operation of the circuit. In a prototype operating example, transistor Q1 was a 2N5087, transistor Q2 is a 2N1539 or a 2N277 or a 2N2082. Transformer 20 in the prototype was a universal plate output transformer such as a TA-9 produced by Essex Stancor and the battery 27 can be two AA cells at 3 volts or a 9 volt radio battery. It is specifically contemplated by the inventors that much smaller transistors and transformers can be used.

As shown in FIG. 2, the circuit is a Darlington common-emitter amplifier with (inverting) transformer coupled output. Since the common-emitter configuration provides both voltage gain and current gain while inverting the waveform, and the transformer provides additional voltage gain at the expense of current gain while again inverting the waveform, the output is in phase with the input with an overall power gain. Since the load provides feedback from the output to the input, it can provide negative resistance in the circuit depending on the magnitude of the feedback and gain of the amplifier. Attention is directed to chapters 15 through 17 of *Functional Circuits and Oscillators* (henceforth abbreviated as FCO) by Herbert J. Reich. Since the $h_{FE}$'s of the two transistors (in the prototype circuit) are respectively 250 to 800 and 35 to 70, and since further the gain of a Darlington is the product of the gains of its elements, the overall low-frequency gain is between the extremes of 9000 and 56000 with most likely region of 17000 to 28000. Furthermore, over the region where the transistors are active, the input resistance is greater than the $h_{ie}$ of the power transistor (at least a few hundred to a thousand ohms) times the $h_{FE}$ of the small signal transistor, thus the input resistance is greater or equal to 50,000 ohms (worst case minimum). Thus negative resistance will be present (i.e., oscillation is possible) provided the feedback resistance (the load) is less than the input resistance multiplied by the gain, which is minimally $50,000 \times 9,000 = 450,000,000$. In other words, oscillation can occur if the load is less than 450 Megohms (worst case) (closer to five to ten thousand Megohms (5,000,000,000) typically). This is assumed in the absence of capacitance, with capacitance present the feedback is increased, a mere 10 picofarads ($10 \times 10^{-12}$ F) provides the same reactance at the operating frequency range. Attention is now drawn to chapters 45 through 46 of FCO, in particular FIG. 157 and the last paragraph of chapter 46, and chapter 48. According to Reich, astable circuits can be generated from voltage-stable (open-circuit-stable) negative resistance elements by adding a small shunt capacitance (or using the internal capacitance of the element) and a series inductance. The inductance is provided in the present invention by the leakage and primary inductances of the transformer. Depending on operating point and susceptance magnitudes anything from square waves to sawtooth to pseudo-sine sawtooths may be generated. A rounded sawtooth is observed in the present invention with very light loading (very little feedback). Attention is directed to chapter 57, chapters 72 through 75 of FCO and the article "Prevent Emitter-Follower Oscillation" in *Electronic Design* 13, June 21, 1976, pp. 110-113. Due to the leakage inductances from emitter to base, and from emitter to collectors, the space-charge and diffusion capacitances of both base-emitter junctions, the space-charge and diffusion capacitances of the collector-base junctions (magnified by the Miller effect) and the fact that all of these quantities (as well as incremental resistances of the transistors) vary with current, voltage, frequency or some combination of more than one of these, the input impedance and feedback impedance are both extremely complex functions (of more than one independent variables). An exact solution is therefore somewhat difficult to obtain. However, when the magnitude of the feedback is increased (slightly lower load impedance), a second mode of oscillation, sinusoidal, appears at a frequency within a couple of octaves of the primary frequency, whenever the instantaneous operating current is in a certain range. The output thus takes on its characteristic, and quite distinctive, waveform.

Copper as well as aluminum electrodes have been used. Decorative silver, gold, as well as other precious metal electrodes are in the contemplation of the inventors. In a highly preferred form of self-protective devices, particularly for use by women as an anti-rape device, the electrodes may be esthetically shaped and in the form of decorative jewelry. Obviously, the disguise of the electrodes can take many forms, and be secured or carried at other places on the person of the user.

Switch 3 (not shown in FIG. 2) may be in the form of an activating or arming switch which merely connects the battery 27 to either the mid-point 25 of transformer 20 or to emitter electrode 29. For example, a user may wish to disable or disarm the entire circuit while in social environments so as to assure that the shock produced is not applied to the body of an acquaintance or friend.

HARMONIC MODE OF OPERATION

Figure 3C:
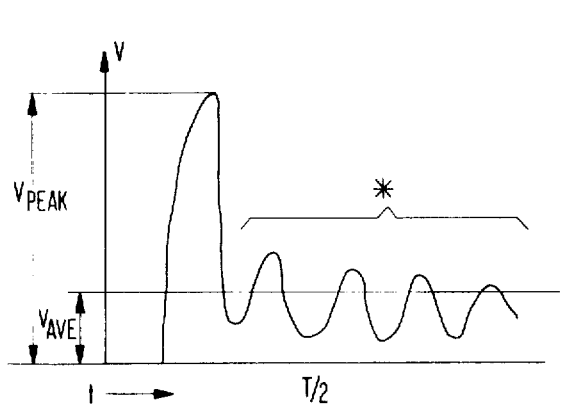
Figure 3C:
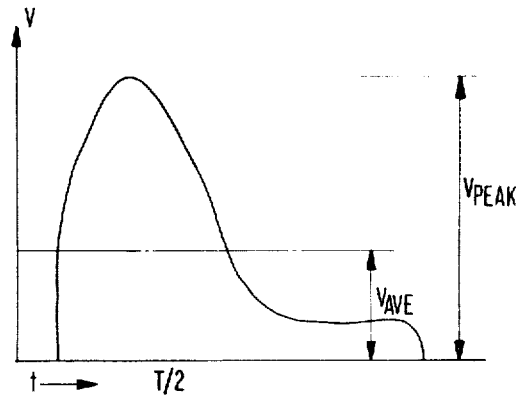
Figure 3C:
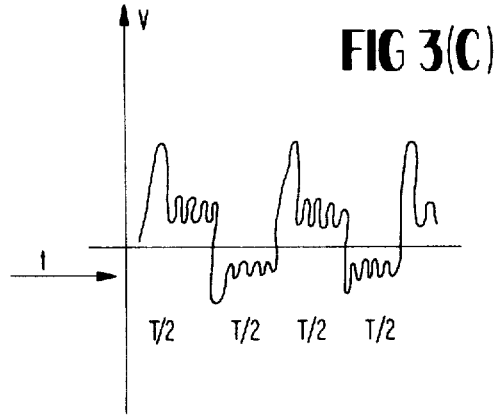

As shown in FIGS. 3(a), 3(b) and 3(c), the various circuit forms of the device all exhibited a sinusoidal (harmonic oscillator) waveform component which is superimposed on a rounded sawtooth. The sawtooth component is produced by a relaxation oscillator mode of the circuit and is locked (synchonized) by the sinusoidal component, whenever the sinusoidal component is present, i.e., in the normal region of operation. Sinusoidal waveforms are produced by harmonic oscillators, which can be grouped into two categories. There are resonant harmonic oscillators and non-resonant harmonic oscillators. The non-resonant harmonic oscillators can be sub-divided further into null-network (including RC and RL bridges) oscillators, phase-shift oscillators, and time-delay (delay-line) oscillators. All of non-resonant harmonic oscillators are characterized by one or more feedback paths arranged such that, at least one frequency, the phase angle around the feedback loop undergoes a total phase shift of $0\pm2\pi n$ radians ($0\pm360n$ degrees) where n is an integer. In the case of the phase shift oscillator, this is normally accomplished by the use of an inverting amplifier followed by a multi-section RC (or rarely RL) filter, with minimally two and usually three sections. The passive filter section then provides, at one frequency, an additional $\pm180$ degrees of phase shift, which with the $-180$ degrees of the inverting amplifier gives a loop phase angle of 0 or $-360$ degrees (Of course the amplitude must be such that at the frequency(s) at which the phase angle meets the conditions set for it the loop gain is greater or equal to unity. The Nyquist stability criterion states for oscillation (harmonic) to occur there must be a frequency at which the loop gain is unity and the net phase angle is 0. (If the loop gain is greater than unity, normally oscillations will increase in amplitude until, due to physical limitations of the amplifier, the loop gain has dropped to unity). In the circuits incorporating the invention, transformer 20 provides, essentially, signal inversion ($-180$ degrees phase shift) over a range of frequencies. Below the lower 3 db frequency the phase angle is leading pure inversion, total angle of phase shift is less than −180 degrees. At end above the upper 3 db frequency the phase angle lags pure inversion resulting in a total phase shift of more than −180 degrees. Since the phase shift is a continuous function of frequency there must be at least one frequency between these two limits at which the Nyquist criterion is satisfied, and by the nature of the physical limitations of the amplifier, if there is more than one, the lowest will be the frequency at which oscillation occurs. Since the input of the amplifier is somewhat lagging in phase reaching an angle of −45 degrees at the frequency $f_{\alpha e}(f_{\alpha e} = f_\beta \approx 5\text{-}15$ KHz for the germanium (Ge) alloy power transistor), which decreases toward zero as frequency decreases; and transformer 20 provides a lead of approximately +45 degrees at its lower 3 db frequency (around 20 Hertz for the transformers in question) which decreases toward zero as frequency increases, both phases referenced to pure inversion, the Nyquist criterion must be satisfied with the decade of frequency from about 20 Hertz upward to 200 Hertz. This agrees with the observed frequency of the harmonic (sinusoidal) component of the output. As shown in FIG. 3(c), the waveform was not symmetric about the time axis, the peak and average voltage differing. This was due to the use of single ended circuits in a relaxation configuration. It was observed that this circuit with various substitutions of components and varying supply voltages will sometimes exhibit the sinusoidal component with clipping of the positive and/or negative peaks for one or more cycles due to saturation effects in the Darlington pair and/or the transformer core and/or cutoff of the Darlington pair. It was further observed that under the circumstances when this condition occurred, the primary effect, an electrically induced shock, was not deleteriously affected.

D.C. BIAS

The circuit is arranged such that positive biasing is derived through the resistive component of the load in a novel and highly efficacious manner. Germanium power transistors being relatively insensitive to D.C. levels and bias conditions, and the 2N5087 being a high gain transistor rated at minimum beta of 250 with a collector current of 0.1 through 10 milliamps, and a minimum beta of 200 at a collector current of 0.01 milliamp (10 micro amp), the combination of the two as a Darlington pair functions quite adequately over an extremely large range of biasing conditions. However, silicon power transistors (which are much less preferred than the germanium types) are much more sensitive to biasing conditions. In the all silicon Darlington or pseudo-Darlington, using the 2N5087 as the input transistor Q1, there is no trouble in obtaining a minimum bias with large resistances in the feedback, however, the power transistor is prone to D.C. saturation as the feedback is increased (feedback resistance lowered). This can be overcome in one of two ways: The first is to balance the increasing positive bias with a fixed negative bias, accomplished by a large 1 to 10 Megohm resistor between points 28 and 33 with the higher resistance values preferred. The second method is to insert a large electrolytic capacitor in series with the output terminal 34 (in line 33), and a standard 100 microfarad 10 volt polarized aluminum electrolytic capacitor was found to work acceptably. In this case, the necessary bias current was obtained through the leakage resistance of the capacitor, which passed the A.C. output unhindered. Non-electrolytic capacitors of high enough capacitance would be prohibitively bulky.

DISCUSSION OF MEASUREMENTS

General Observation

The final circuit configuration, by configuration and its high gain, is sensitive to leakage admittance in the matter of initiating and maintaining oscillation. In a breadboard form, for example, it was possible to initiate oscillation by placing a hand or medium sized metal object within 2 or 3 inches of the layout, similarly twisting the output leads into a few turn 'gimmick' capacitor was sufficient to initiate oscillation. Occasionally, once oscillation began, it would be maintained even after conditions were returned to initial form.

The output waveform is, in contrast, relatively insensitive to loading effects. An 'unloaded' (FIG. 3(b)) waveform was observed with the scope alone or with the scope shunted by the VOM and/or a 7 Megohm ($7 \times 10^6$ ohms) linear potentiometer set to maximum resistance. In addition, it was observed to be insensitive to capacitive loading up to and including 1.5 nF (1500 pF). As the shunt resistance on the output was made lower in resistance, the output waveform changed in character until a 'loaded' waveform was reached. This waveform then remained qualitatively unchanged until output loading was enough to stop oscillation. Capacitive loading of the same amount as in the unloaded case again had no effect.

The waveforms in both the loaded and unloaded cases were observed to show, qualitatively, effectively no variation (i.e., no variation in shape) with changes in operating level or fundamental frequency.

QUANTITATIVE DATA (a) Frequency

The fundamental frequency can be made to vary by adjusting the circuit elements or, to a lesser extent, by changing the output loading, normally, it is observed to lie within a decade of 100 Hz (10 to 1000 Hz). During operation for the purposes currently being exploited, it is usually adjusted to stay within the active 45 to 90 Hz.

(b) Voltage

Unloaded output voltages (average by rms weighting circuit, 50 v and 250 v scales primarily, meter set for A.C.), have been observed as low as approximately 10 volts and as high as 5 kv (5000 volts), however, outside of extreme areas of operation the averaged output voltage was observed to lie between 20 volts and 90 volts. This normal range is observed over a large range of loading conditions, from unloaded to just short of termination of oscillation. The peak to average voltage ratio was determined to be greater than 3 with the VOM and a neon bulb, and was observed to range from 4 to 7 with the scope, depending on circuit constants. The apparent disparity is understandable when one considers that a neon bulb tends to act as a peak clipping element due to its non-linear resistance.

The object of a device used as in a self-protection system, is to induce a painful but harmless electric shock in the area of contact of a mammalian organism. In this case, the method used by existing devices (the 'cattle-prod', etc.) is to use high voltage, either direct or alternating current, to induce current flow in the contacted area. Damage, below the threshold necessary to cause burns, results from the current flow, and causes painful sensations since the sensory nerves react to the organic damage. Even though of a transient nature, the organic damage is not necessary and highly undesirable as this is wasteful of power, and critical of adjustment if more permanent damage is to be avoided.

The present invention generates, under load, a waveform which breaks down the skin resistance (generally between a few thousand and a million or two ohms) and then couples directly into the sensory nerves (via this transient low resistance path), a signal within the passband of the nerves. This means much lower power can be used while achieving a greater, more painful shock. Adjustment is much less critical as overload power levels to the nerves of several orders above what is normally presented by the present circuit are still well below levels causing damage. Placement of contacts to a sensitive area of the body is not necessary, as an interference signal, coupled into the nervous system, affects to a lesser degree all areas connected to the same nerve trunk. This effect has been described by test subjects touching the output electrodes 15 and 16 with the index and middle fingers of one hand as "it crawled up my arm" and "I felt it up to my shoulder".

The basic objectives of the invention are to provide a minimal componentry power oscillator which functions by taking advantage of the non-ideal characteristics of the components, such as hysteresis and saturation in the inductive components and the phase/amplitude versus frequency response in the gain elements to produce stable, within a wide range, non-sinusoidal, low-frequency oscillations. The unique feedback configuration achieves a self-adjusting output. Because of the unique circuit configuration it does not require wetted electrodes to initiate oscillation.

Moreover, since the oscillator is quiescent (even when 'activated' or 'armed' by the closing of switch 13) the only power consumed is the leakage current of the output transistor. In its more preferred form the only circuit components required are those shown in FIG. 2, transistor Q2 being a germanium type power transistor so the circuit may be reduced to extremely small physical proportions or dimensions with transformer 20 and battery 27 being the largest components. The electrodes 15 and 16 may be deposited in various forms on a substrate and if crossovers are desired, a thin insulating layer may be used.

It is obvious that various other modifications and changes may be incorporated in the invention without departing from the spirit and scope thereof as set forth in the claims appended hereto.

We claim:

1. A voltage step-up circuit for delivering a stepped up voltage to a pair of output electrodes comprising: a normally quiescent oscillator circuit constituted by an inverting high gain transistor amplifier, said transistor amplifier having an emitter-collector output circuit and a base-emitter input circuit; a source of unidirectional voltage; an inverting voltage step-up transformer having a low voltage primary winding and a high voltage secondary winding; a first series circuit constituted by said source of unidirectional voltage, said emitter-collector circuit and said primary winding; and a second series circuit feedback arrangement constituted by said secondary winding, said pair of output electrodes, said base-emitter input circuit and said source of unidirectional voltage; said quiescent circuit being rendered oscillatory solely upon the presence of a high resistance load across said output electrodes.

2. The invention defined in claim 1 wherein said inverting transistor amplifier is a Darlington connected transistor pair.

3. The invention defined in claim 2 wherein the output transistor of said Darlington pair is a germanium power transistor.

4. The invention defined in claim 3 including an arming switch connected in series circuit with said source of unidirectional voltage.

5. A voltage step-up circuit comprising: a normally quiescent oscillator circuit which consists of a pair of output electrodes, an inverting voltage step-up transformer having a primary winding and a stepped up voltage feedback winding, a low voltage battery, and an inverting transistor amplifier having an emitter-collector circuit and an emitter-base circuit; conductor means connecting said primary winding of said transformer, said low voltage battery and the emitter-collector circuit of said inverting transistor amplifier in a series circuit; and further conductor means connecting said pair of output electrodes, said feedback winding, said battery and the emitter-base circuit of said transistor amplifier in a further series circuit; said further series circuit being completed solely on the presence of a high impedance load between said pair of output electrodes, whereupon the oscillator circuit becomes oscillatory and a stepped up voltage is applied across said output electrodes.

* * * * *